United States Patent
Yukawa (10) Patent No.: US 12,247,876 B2
(45) Date of Patent: Mar. 11, 2025

(54) SENSING DEVICE

(71) Applicant: Japan Display Inc., Tokyo (JP)

(72) Inventor: Motochika Yukawa, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 18/585,142

(22) Filed: Feb. 23, 2024

(65) Prior Publication Data

US 2024/0295435 A1 Sep. 5, 2024

(30) Foreign Application Priority Data

Mar. 3, 2023 (JP) .................. 2023-032877

(51) Int. Cl.
 *G01J 1/44* (2006.01)
 *G01J 1/04* (2006.01)
 *A61B 5/00* (2006.01)

(52) U.S. Cl.
 CPC .............. *G01J 1/44* (2013.01); *G01J 1/0407* (2013.01); *A61B 5/0059* (2013.01); *G01J 2001/446* (2013.01)

(58) Field of Classification Search
 CPC ...... G01J 1/44; G01J 1/0407; G01J 2001/446; A61B 5/0059
 See application file for complete search history.

(56) References Cited

U.S. PATENT DOCUMENTS

| | | | |
|---|---|---|---|
| 2019/0080668 A1* | 3/2019 | Holenarsipur | H04N 23/20 |
| 2022/0238825 A1 | 7/2022 | Mochizuki et al. | |
| 2022/0240862 A1* | 8/2022 | Lee | A61B 5/0059 |
| 2023/0178574 A1 | 6/2023 | Tago et al. | |

FOREIGN PATENT DOCUMENTS

| | | |
|---|---|---|
| JP | 2021-68793 A | 4/2021 |
| JP | 2022-23667 A | 2/2022 |

* cited by examiner

*Primary Examiner* — Georgia Y Epps
*Assistant Examiner* — Don J Williams
(74) *Attorney, Agent, or Firm* — Michael Best & Friedrich LLP (57) ABSTRACT

A sensing device 1 includes a light detection sensor that includes a lower electrode, an organic layer provided above the lower electrode, and an upper electrode provided above the organic layer, a sealing structure that includes at least a first inorganic layer provided above the light detection sensor and a first resin layer provided above the first inorganic layer, and an optical filter that is provided above the light detection sensor and blocks a part of light incident on the light detection sensor using at least one of the first inorganic layer or the first resin layer as a layer thickness adjustment layer. An end portion of the first inorganic layer is positioned outward of an end portion of the organic layer.

17 Claims, 11 Drawing Sheets

SENSING DEVICE

CROSS-REFERENCE TO RELATED APPLICATION

The present application claims priority from Japanese patent application No. 2023-032877 filed on Mar. 3, 2023, the content of which is hereby incorporated by reference into this application.

BACKGROUND OF THE INVENTION

1. Field of the Invention

The present invention relates to a sensing device.

2. Description of the Related Art

JP2021-68793A discloses an optical sensor device using an organic photo diode (OPD). JP2022-23667A discloses a collimator as an optical filter that transmits and blocks the components of the light reflected by the detection object, such as a finger, where the components of light traveling in the normal direction are transmitted toward the photodiodes, and the components of the light traveling in the oblique directions are blocked. The collimator used in this manner can inhibit crosstalk caused by the components of light traveling in the oblique direction. This can inhibit blur in a detected image, thereby improving detection accuracy.

The collimator needs to have a thickness sufficient to block the components of light traveling in the oblique direction, and is thicker than a photodiode element. As such, with the collimator, a device is increased in overall thickness.

SUMMARY OF THE INVENTION

One or more embodiments of the present invention have been conceived in view of the above, and an object thereof is to provide a sensing device having a function as an optical filter and capable of reducing the thickness.

Solution to Problem

In order to solve the above described problems, a sensing device according to an aspect of the present invention includes a light detection sensor that receives light reflected by a detection object or light transmitted through the detection object and includes a lower electrode, an organic layer provided above the lower electrode, and an upper electrode provided above the organic layer, a sealing structure that includes at least a first inorganic layer provided above the light detection sensor and a first resin layer provided above the first inorganic layer, and an optical filter that is provided above the light detection sensor and blocks a part of light incident on the light detection sensor using at least one of the first inorganic layer or the first resin layer as a layer thickness adjustment layer, wherein an end portion of the first inorganic layer is positioned outward of an end portion of the organic layer.

DETAILED DESCRIPTION OF THE INVENTION

Embodiments of the present invention will be described in detail referring to the drawings. In this regard, the present invention is not to be limited to the embodiments described below, and can be changed as appropriate without departing from the spirit of the invention.

The accompanying drawings may schematically illustrate widths, thicknesses, shapes, or other characteristics of each part for clarity of illustration, compared to actual configurations. However, such a schematic illustration is merely an example and not intended to limit the present invention. In this specification and the drawings, some elements identical or similar to those shown previously are denoted by the same reference signs as the previously shown elements, and thus repetitive detailed descriptions of them may be omitted as appropriate.

Furthermore, in the detailed description of the present invention, when defining the positional relationship between a certain component and another component, the terms "above" and "below" include not only the case where located directly above or below the certain component, but also the case where other components are further interposed therebetween unless otherwise specified.

In the following description, the "outer side" is a side close to the outer edge of a sensing device 1. In the following description, the "end portion" of each layer is a portion of each layer that is close to the outer edge of the sensing device 1 and includes an end surface.

[Summary of Sensing Device]

The sensing device 1 according to the present embodiment may detect light reflected by a finger of a user, which is a detection object pensioned on a microlens 360 to be described later or light transmitted through the finger of the user, thereby detecting biological information such as fingerprint information. The sensing device 1 also functions as a collimator, which is an optical filter for inhibiting a decrease of contrast due to crosstalk. The sensing device 1 may include a light source that irradiates the detection object with light so as to obtain reflected light or transmitted light used for sensing, but this will not be described in the present embodiment.

Figure 1A:
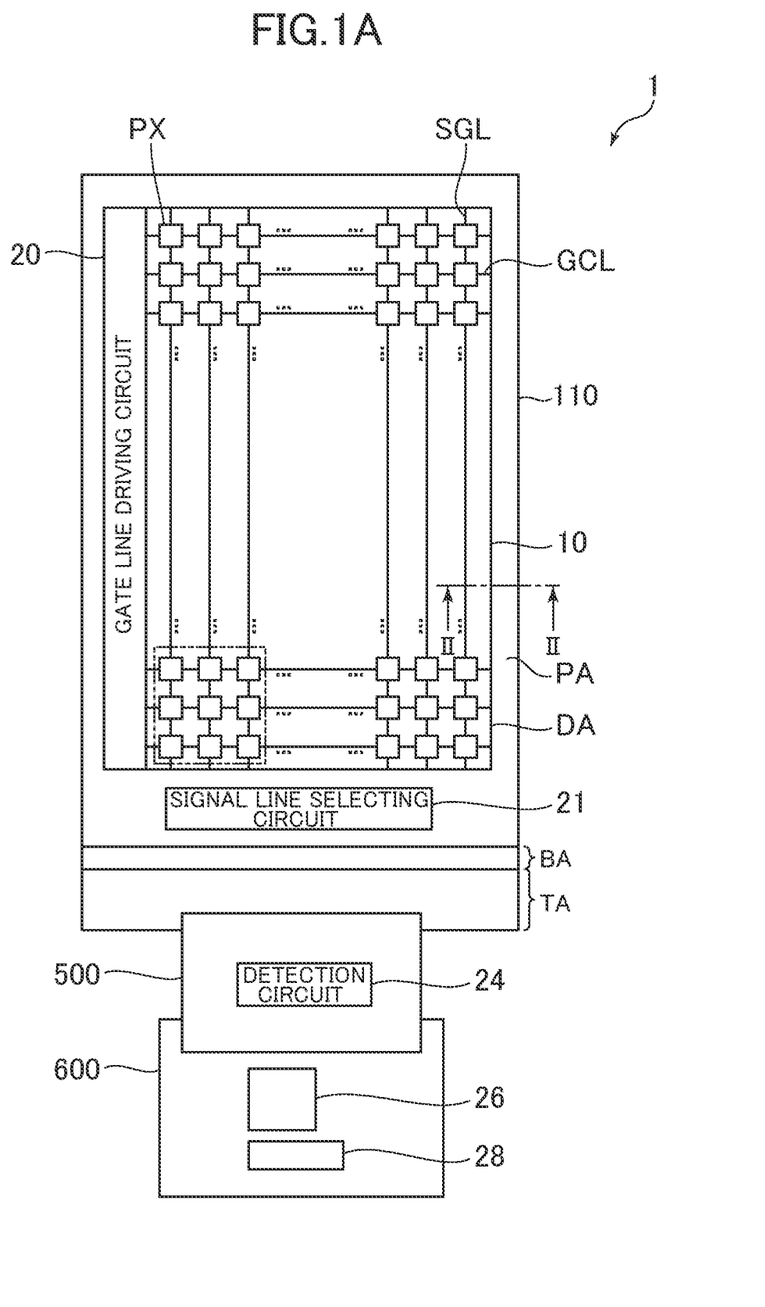
FIG. 1A is a schematic plan view of a sensing device according to the present embodiment.
Figure 1B:
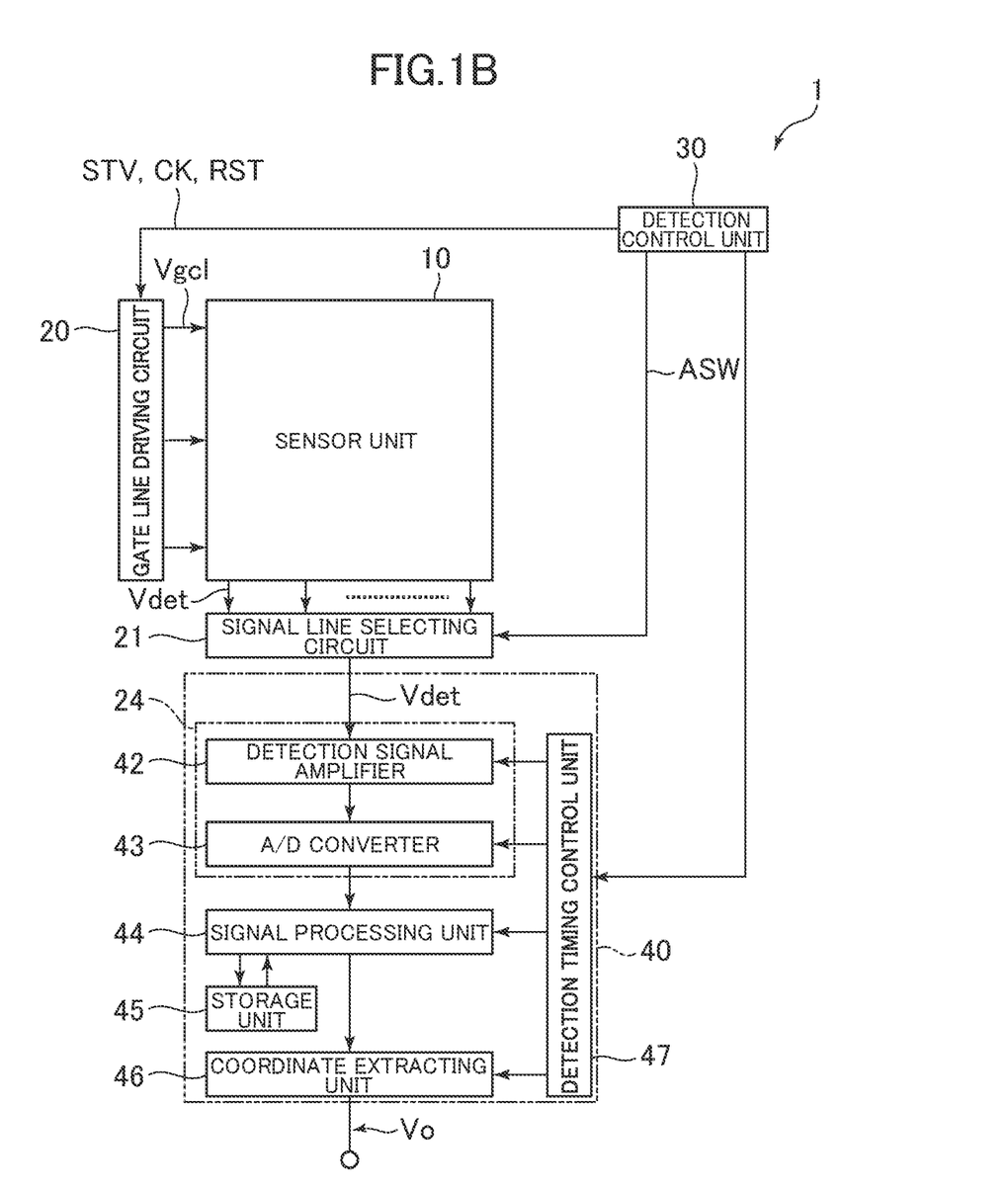
FIG. 1B is a block diagram showing a configuration and functions of the sensing device according to the present embodiment.

FIG. 1A is a schematic plan view of a sensing device according to the present embodiment. FIG. 1B is a block diagram showing a configuration and functions of the sensing device according to the present embodiment.

As shown in FIG. 1A, the sensing device 1 includes a substrate 110, a sensor unit 10, a gate line driving circuit 20, a signal line selecting circuit 21, a detection circuit 24, a control circuit 26, and a power supply circuit 28.

A control substrate 600 is electrically connected to the substrate 110 via a flexible printed board 500. The flexible printed board 500 includes the detection circuit 24. The control substrate 600 includes the control circuit 26 and the power supply circuit 28. The control circuit 26 is a field programmable gate array (FPGA), for example. The control circuit 26 supplies control signals to the sensor unit 10, the gate line driving circuit 20, and the signal line selecting circuit 21 so as to control the detection operation of the sensor unit 10. The power supply circuit 28 supplies a power supply voltage to the sensor unit 10, the gate line driving circuit 20, and the signal line selecting circuit 21.

The sensing device 1 includes a detection area DA and a frame area PA. The detection area DA is an area in which the sensor unit 10 is provided. The frame area PA is positioned outside the detection area DA and is not provided with the sensor unit 10. In other words, the frame area PA is an area between the end portion of the detection area DA and the end portion of the substrate 110. The frame area PA includes a bending area BA and a terminal area TA. The bending area BA and the terminal area TA are provided at one end of the frame area PA. Wires connected to the detection area DA are disposed in the bending area BA and the terminal area TA. The substrate 110 and the flexible printed board 500 are connected in the terminal area TA.

The sensor unit 10 includes a plurality of pixels PX and receives light from the detection object. The pixels PX are disposed in a matrix in the detection area DA. The pixels PX include light detection sensors, which are photodiodes, and respectively output electric signals corresponding to light irradiating the respective photodiodes. Each pixel PX outputs an electric signal corresponding to the light irradiating the pixel PX to the signal line selecting circuit 21 as a detection signal Vdet. The sensing device 1 may be capable of detecting biological data, such as a blood vessel image of a finger and a palm, a pulse wave, a pulse, and a blood-oxygen saturation, based on the detection signal Vdet from each pixel PX. Each pixel PX performs detection in accordance with a gate drive signal Vgcl supplied from the gate line driving circuit 20.

The gate line driving circuit 20 and the signal line selecting circuit 21 are provided in the frame area PA. Specifically, as shown in FIG. 1A, the gate line driving circuit 20 is provided in an area of the frame area PA extending along the extension direction of the signal line SGL. The signal line selecting circuit 21 is provided in an area of the frame area PA extending along the extension direction of the gate line GCL, and is provided between the sensor unit 10 and the bending area BA.

As shown in FIG. 1B, the sensing device 1 further includes a detection control unit 30 and a detection unit 40. Some or all of the functions of the detection control unit 30 are included in the control circuit 26. Further, some or all of the functions of the detection unit 40 other than the detection circuit 24 are included in the control circuit 26.

The detection control unit 30 is a circuit that supplies control signals to the gate line driving circuit 20, the signal line selecting circuit 21, and the detection unit 40, and controls these operations. The detection control unit 30 supplies control signals, such as a start signal STV, a clock signal CK, and a reset signal RST, to the gate line driving circuit 20. The detection control unit 30 supplies control signals, such as a selection signal ASW, to the signal line selecting circuit 21. The gate line driving circuit 20 drives the gate line GCL based on the control signals. The gate line driving circuit 20 sequentially or simultaneously selects a plurality of gate lines GCL, and supplies a gate drive signal Vgcl to the selected gate line GCL. In this manner, the gate line driving circuit 20 selects a pixel PX connected to the gate line GCL. The signal line selecting circuit 21 is a switching circuit that sequentially or simultaneously selects a plurality of signal lines SGL. The signal line selecting circuit 21 is a multiplexer, for example. The signal line selecting circuit 21 connects the selected signal line SGL with the detection circuit 24 based on the selection signal ASW supplied from the detection control unit 30. This enables the signal line selecting circuit 21 to output a detection signal Vdet of the pixel PX to the detection unit 40.

The detection unit 40 includes the detection circuit 24, a signal processing unit 44, a storage unit 45, a coordinate extracting unit 46, and a detection timing control unit 47. The detection timing control unit 47 controls the detection circuit 24, the signal processing unit 44, and the coordinate extracting unit 46 to operate in synchronization based on the control signal supplied from the detection control unit 30.

The detection circuit 24 is an analog front end circuit (AFE), for example. The detection circuit 24 is a signal processing circuit having at least functions of a detection signal amplifier 42 and an A/D converter 43. The detection signal amplifier 42 amplifies the detection signal Vdet. The A/D converter 43 converts an analog signal from the detected signal amplifier 42 into a digital signal. The signal processing unit 44 is a logic circuit that detects a predetermined physical quantity entered into the sensor unit 10 based on the output signal of the detection circuit 24. When a detection target, such as a finger and a palm, comes into contact with or is close to the detection surface, the signal processing unit 44 detects unevenness of the surface of the finger and the palm based on the signal from the detection circuit 24. Further, the signal processing unit 44 detects biological data, such as a blood vessel image of a finger and a palm, a pulse wave, a pulse, and a blood-oxygen saturation, based on a signal from the detection circuit 24. The storage unit 45 temporarily stores the signal calculated by the signal processing unit 44. The storage unit 45 may be a random access memory (RAM) or a register circuit, for example. The coordinate extracting unit 46 is a logic circuit that obtains detection coordinates of unevenness of a surface of a finger and a palm, for example, when the signal processing unit 44 detects contact or approach of the finger or the palm. The coordinate extracting unit 46 is a logic circuit that obtains detection coordinates of blood vessels of a finger and a palm, for example. The coordinate extracting unit 46 combines detection signals Vdet from the respective pixels PX of the sensor unit 10 to generate two-dimensional information indicating the shape of the unevenness of the surface of the finger and the palm, for example. The coordinate extracting unit 46 may not calculate the detection coordinates but output the detection signal Vdet as the sensor output Vo.

[Laminate Structure of Sensing Device]

Figure 2:
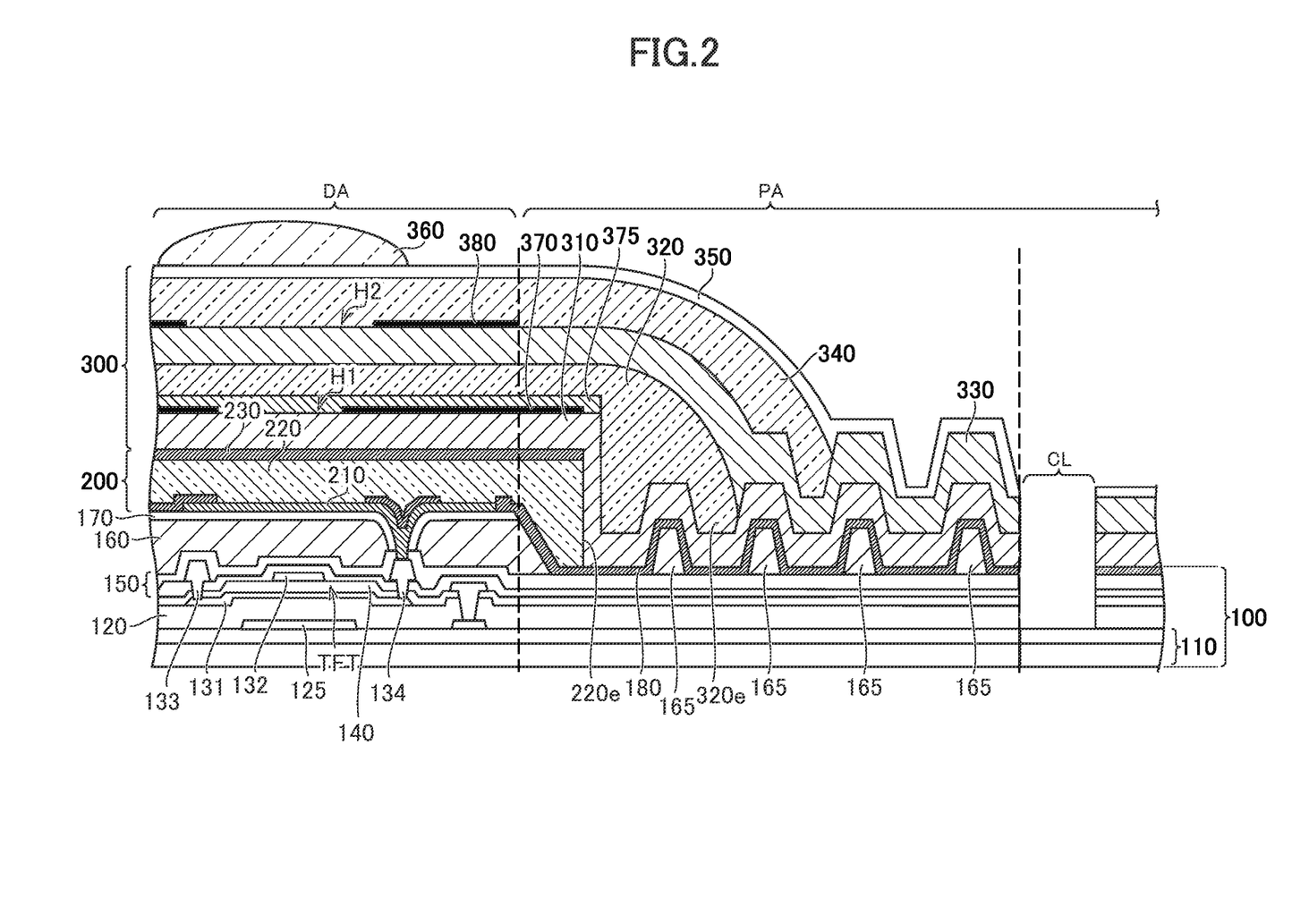
FIG. 2 is a schematic cross-sectional view of the sensing device taken along the line II-II in FIG. 1A.

FIG. 2 is a schematic cross-sectional view of the sensing device 1 taken along the line II-II in FIG. 1A. FIG. 2 shows a part of the detection area DA near the end portion and a part of the frame area PA. In FIG. 2, hatching of some layers is omitted for clarity of the cross-sectional structure (the same applies to FIGS. 3 to 7 described later).

As shown in FIG. 2, the sensing device 1 includes a TFT layer 100 including a thin film transistor TFT, an OPD layer 200 provided above the TFT layer 100, and a sealing structure 300 provided above the OPD layer 200.

The TFT layer 100 includes the substrate 110 and a barrier inorganic layer 120 provided above the substrate 110. For example, the substrate 110 may have a two-layer structure of a glass substrate and a resin substrate provided thereon. The resin substrate may be formed of polyimide, for example. However, the present invention is not limited thereto, and the substrate 110 does not have a glass substrate and may be formed of only a flexible resin substrate. The barrier inorganic layer 120 may have a laminate structure including a plurality of layers. The TFT layer 100 may have an additional layer 125 in accordance with a position where the thin film transistor TFT is formed.

The thin film transistor TFT includes a semiconductor layer 131, a gate electrode 132, a source electrode 133, and a drain electrode 134. A gate insulating layer 140 is provided between the semiconductor layer 131 and the gate electrode 132. A silicon oxide layer may be used as the gate insulating layer 140. An interlayer insulating layer 150 is formed on the gate electrode 132. The interlayer insulating layer 150 may have a laminate structure of a silicon nitride layer and a silicon oxide layer.

A flattening layer 160 is provided to cover the interlayer insulating layer 150. The flattening layer 160 may be made of a resin having excellent surface flatness, such as photosensitive acrylic. The flattening layer 160 may be removed at a part that electrically connects the OPD layer 200 and the TFT layer 100. The end portions of the flattening layer 160 may be positioned in the frame area PA. The flattening layer 160 may be partially removed in the frame area PA. An insulating layer 170 may be provided above the flattening layer 160. Further, an inorganic insulating layer 180 made of an inorganic material may be provided above the insulating layer 170. The inorganic insulating layer 180 may also be provided above the lower electrode 210 included in the OPD layer 200 so as to expose the lower electrode 210. The inorganic insulating layer 180 may be provided above the flattening layer 160 in the frame area PA.

The OPD layer 200 includes a light detection sensor. The light detection sensor includes a lower electrode 210 provided above the insulating layer 170, an organic layer 220 provided above the lower electrode 210, and an upper electrode 230 provided above the organic layer 220. The organic layer 220 functions as a photoelectric conversion layer. The upper electrode 230 is a common electrode provided across the pixels. The lower electrode 210 is provided corresponding to each pixel, and is electrically connected to the drain electrode 134 of the TFT layer 100.

The sealing structure 300 includes a first inorganic layer 310 provided above the upper electrode 230, a first transparent resin layer 320, which is a first resin layer, provided above the first inorganic layer 310, a second inorganic layer 330 provided above a first transparent resin layer 320, and a second transparent resin layer 340, which is a second resin layer provided above the second inorganic layer 330. The first inorganic layer 310, the first transparent resin layer 320, the second inorganic layer 330, and the second transparent resin layer 340 may have optical transparency.

The end portion of the first inorganic layer 310 (not shown in FIG. 2) is positioned outward of an end portion 220e of the organic layer 220. That is, the end portion of the first inorganic layer 310 is positioned in the frame area PA. The first inorganic layer 310 is in contact with the end portion 220e of the organic layer 220. The first inorganic layer 310 is in contact with the inorganic insulating layer 180 on the outside of the end portion 220e of the organic layer 220.

The second inorganic layer 330 is in contact with the first inorganic layer 310 in the frame area PA. As described above, the layers made of the inorganic material prevent moisture from entering the organic layer 220 from the outside in the sealing structure 300.

As shown in FIG. 2, the flattening layer 160 and the inorganic insulating layer 180 formed along the flattening layer 160 form a wall portion 165 in the frame area PA. The wall portion 165 may be formed when the flattening layer 160 formed in the frame area PA is partially removed and the inorganic insulating layer 180 is provided above the remaining portion of the flattening layer 160. The wall portion 165 is formed so as to prevent the resin material forming the OPD layer 200 and the sealing structure 300 from leaking out of the frame area PA when such layers are formed. FIG. 2 shows an example in which four wall portions 165 are formed side by side toward the outside, although the number of wall portions 165 is not limited thereto. Alternatively, the wall portion 165 may not be provided. That is, the flattening layer 160 may not be provided in the frame area PA.

As shown in FIG. 2, in the present embodiment, the first inorganic layer 310 and the second inorganic layer 330 are formed along the shape of the wall portions 165 in the frame area PA. As described above, the inorganic layer is formed along the unevenness formed by a plurality of wall portions 165, whereby the shielding property against moisture is further improved. Further, as shown in FIG. 2, the end portion 320e of the first transparent resin layer 320 may be covered with the second inorganic layer 330.

In the present embodiment, the sealing structure 300 has the function to cover the OPD layer 200 so as to prevent moisture from entering the organic layer 220 from the outside, and also has the function as a collimator, which is an optical filter. As such, the sealing structure 300 includes a foundation layer 350 provided above the second transparent resin layer 340, a microlens 360 provided above the foundation layer 350, a first light shielding layer 370 provided above the first inorganic layer 310, and a second light shielding layer 380 provided above the second inorganic layer 330. The first transparent resin layer 320 and the second transparent resin layer 340 may be made of a material having high transmittance and low moisture permeability.

The foundation layer 350 may be made of an organic material. The organic material used as the foundation layer 350 improves adhesion to the microlens 360. Further, processability of the microlens 360 is improved. The foundation layer 350 may be made of an inorganic material. The organic material used as the foundation layer 350 further improves the shielding property against moisture. The foundation layer 350 may also function as a layer for adjusting the focal length of the collimator.

A first opening H1 is formed in the first light shielding layer 370 so as to allow light to enter the OPD layer 200. A second opening H2 is formed in the second light shielding layer 380 so as to allow light to enter the OPD layer 200. The width of the second opening H2 may be larger than the width of the first opening H1. The first opening H1 and the second opening H2 may be circular in a plan view. In this case, the diameter of the second opening H2 may be larger than the diameter of the first opening H1 in a plan view.

The first light shielding layer 370 and the second light shielding layer 380 may be made of a resin or a metal that blocks light incident thereon. For example, the first light shielding layer 370 formed of a thin-film metal facilitates processing and forming a small width opening. The second light shielding layer 380 is made of a thick black resin, which serves to block unnecessary light from the outside.

The first light shielding layer 370 and the second light shielding layer 380 allow a component of light that travels in the normal direction among the light reflected by the detection object, such as a finger, to enter the OPD layer 200 through the first opening H1 and the second opening H2, and shield a component of light that travels in the oblique direction.

The microlens 360 is a convex lens. The microlens 360 may be circular in a plan view and have a larger diameter than the second opening H2 and may be provided so as to overlap with the second opening H2 in a plan view. The present invention is not limited thereto, and the microlens 360 may be disposed such that at least a part of the microlens 360 overlaps the first opening H1 and the second opening H2 in a plan view. A part of the light reflected by the detection object, such as a finger, is collected by the microlens 360 and passes through the second opening H2 and the first opening H1 to enter the OPD layer 200.

As shown in FIG. 2, the sealing structure 300 may include a filter layer 375 on the first light shielding layer 370 for blocking light of a specific wavelength. The filter layer 375 may also be provided inside the first opening H1 of the first light shielding layer 370. The filter layer 375 may be an IR (infrared rays) cut filter, for example.

As described above, the sealing structure 300 has the function of an optical filter in the present embodiment. In other words, the first inorganic layer 310, the first transparent resin layer 320, the second inorganic layer 330, and the second transparent resin layer 340, which function only as a layer thickness adjustment layer for ensuring the light shielding property in the optical filter, are allowed to have a function of preventing moisture from entering the organic layer 220 from the outside. As such, the thickness of the sensing device 1 can be reduced as compared with a configuration in which an optical filter is separately laminated. Further, another function is provided to the layer constituting the optical filter, and thus the layer constituting the optical filter can be effectively used.

FIG. 2 shows an example in which a cut line CL is formed so as to surround the detection area DA in the frame area PA. The layers above the substrate 110 are removed in the cut line CL. However, the configuration of the frame area PA is not limited to the example shown in FIG. 2.

[First Modification]

Figure 3:
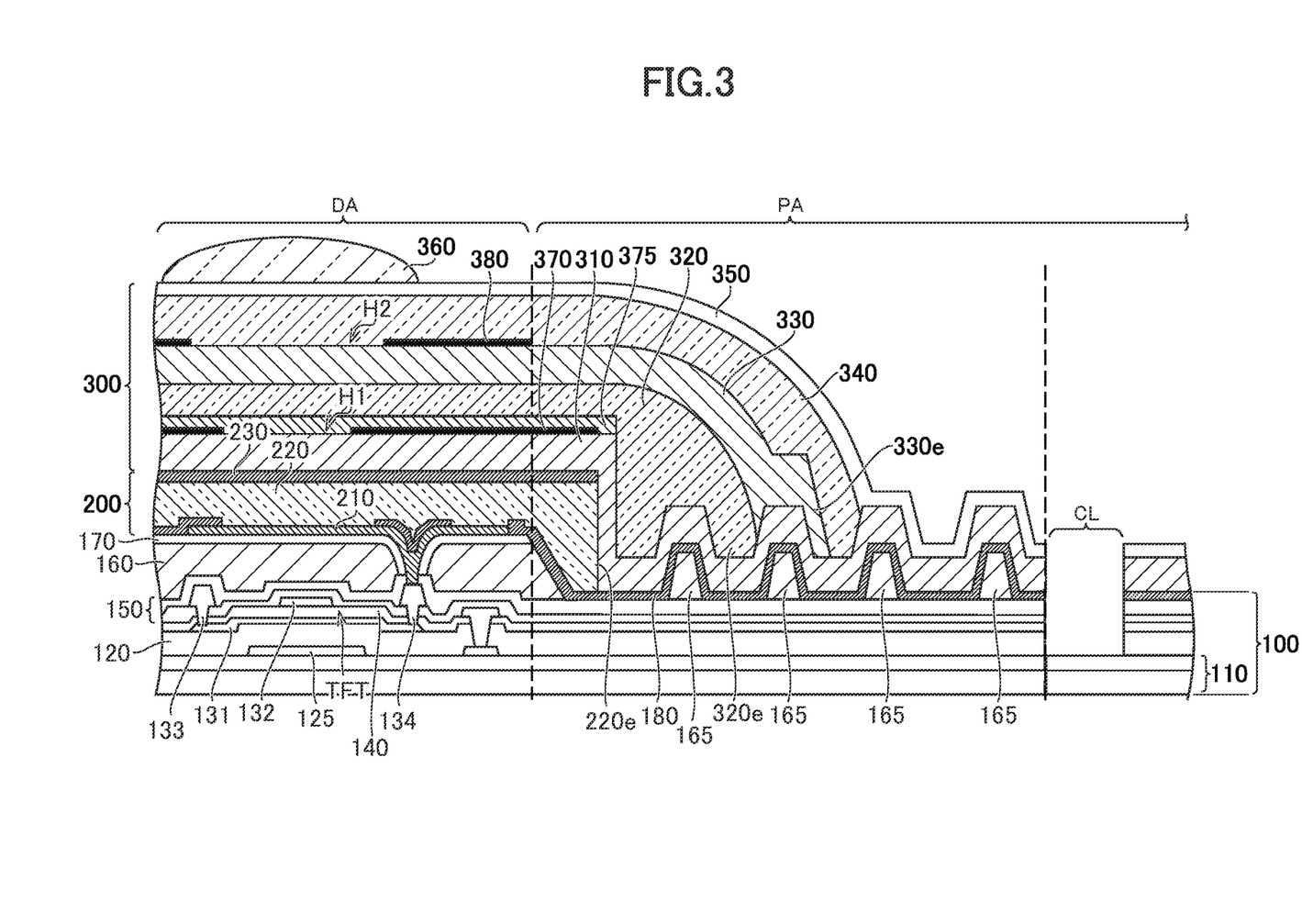
FIG. 3 is a cross-sectional view of a sensing device according to a first modification.

Next, referring to FIG. 3, a sensing device according to the first modification of the present embodiment will be described. FIG. 3 is a cross-sectional view of a sensing device according to the first modification. FIG. 3 shows a part corresponding to the cross-sectional view shown in FIG. 2. The layers having the same functions as the layers described with reference to FIG. 2 are denoted by the same reference signs, and the detailed explanation thereof is omitted. In the following, the configuration different from the configuration described with reference to FIG. 2 will be mainly described.

In FIG. 2, the second inorganic layer 330 extends outward from the cut line CL in the frame area PA, although as shown in FIG. 3, an example of the first modification will be described in which the end portion 330e of the second inorganic layer 330 is in contact with the first inorganic layer 310 inside the cut line CL. In the first modification, the foundation layer 350 may be made of an inorganic material.

In the first modification, the end portion 330e of the second inorganic layer 330 is in contact with the first inorganic layer 310 in the frame area PA. The foundation layer 350 is in contact with the first inorganic layer 310 in the frame area PA. That is, the foundation layer 350 is in contact with the first inorganic layer 310 outside the end portion 330e of the second inorganic layer 330 in the frame area PA. Such a configuration can prevent moisture from entering the organic layer 220 from the outside. As shown in FIG. 3, the end portion 320e of the first transparent resin layer 320 may be covered with the end portion 330e of the second inorganic layer 330.

[Second Modification]

Figure 4:
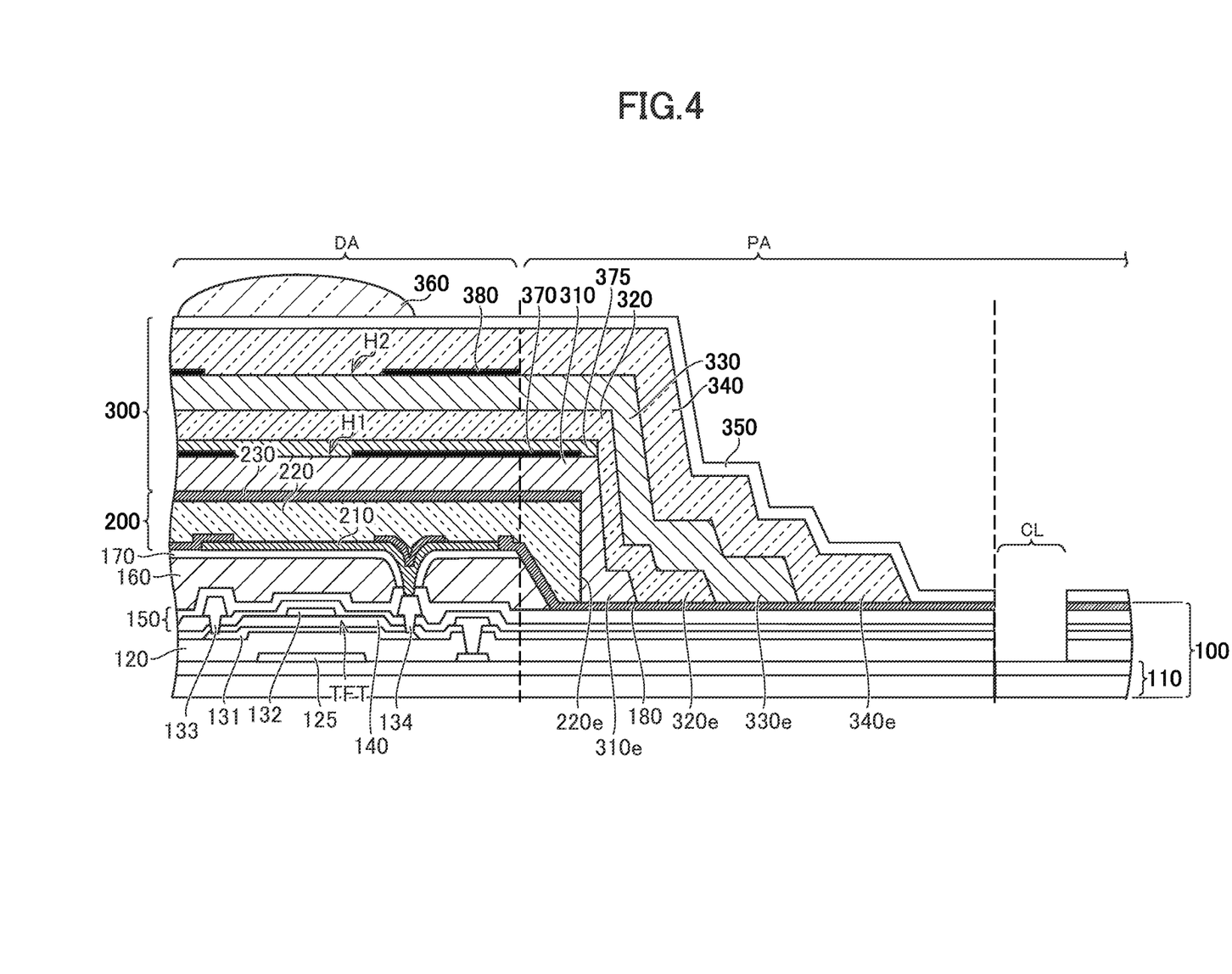
FIG. 4 is a cross-sectional view of a sensing device according to a second modification.

Next, referring to FIG. 4, a sensing device according to the second modification of the present embodiment will be described. FIG. 4 is a cross-sectional view of a sensing device according to the second modification. FIG. 4 shows a part corresponding to the cross-sectional view shown in FIG. 2. The layers having the same functions as the layers described with reference to FIG. 2 are denoted by the same reference signs, and the detailed explanation thereof is omitted. In the following, the configuration different from the configuration described with reference to FIG. 2 will be mainly described.

In the second modification, the wall portion 165 is not formed in the frame area PA. The inorganic insulating layer 180 is provided in contact with the interlayer insulating layer 150 in the frame area PA.

The first inorganic layer 310, the first transparent resin layer 320, the second inorganic layer 330, the second transparent resin layer 340, and the foundation layer 350 are laminated so as to be gradually lowered toward the outside in the frame area PA.

The end portion 310e of the first inorganic layer 310, the end portion 320e of the first transparent resin layer 320, the end portion 330e of the second inorganic layer 330, the end portion 340e of the second transparent resin layer 340, and the end portion of the foundation layer 350 are positioned outward of the end portion 220e of the organic layer 220. The end portion 310e of the first inorganic layer 310, the end portion 320e of the first transparent resin layer 320, the end portion 330e of the second inorganic layer 330, the end portion 340e of the second transparent resin layer 340, and the end portion of the foundation layer 350 are positioned in the frame area PA and in contact with the inorganic insulating layer 180. The foundation layer 350 may be made of an inorganic material in the second modification.

In the second modification described above, similarly to the embodiment and the first modification, the configuration is employed in which the sealing structure 300 covers the end portion 220e of the organic layer 220. Further, the foundation layer 350 made of an inorganic material is in contact with the inorganic insulating layer 180. Such configurations can inhibit moisture from entering the organic layer 220 from the outside. The wall portion 165 shown in FIG. 2 is not provided, and thus the structure of the sealing structure 300 is simple in the frame area PA and can be easily molded.

[Other Modifications]

Figure 5:
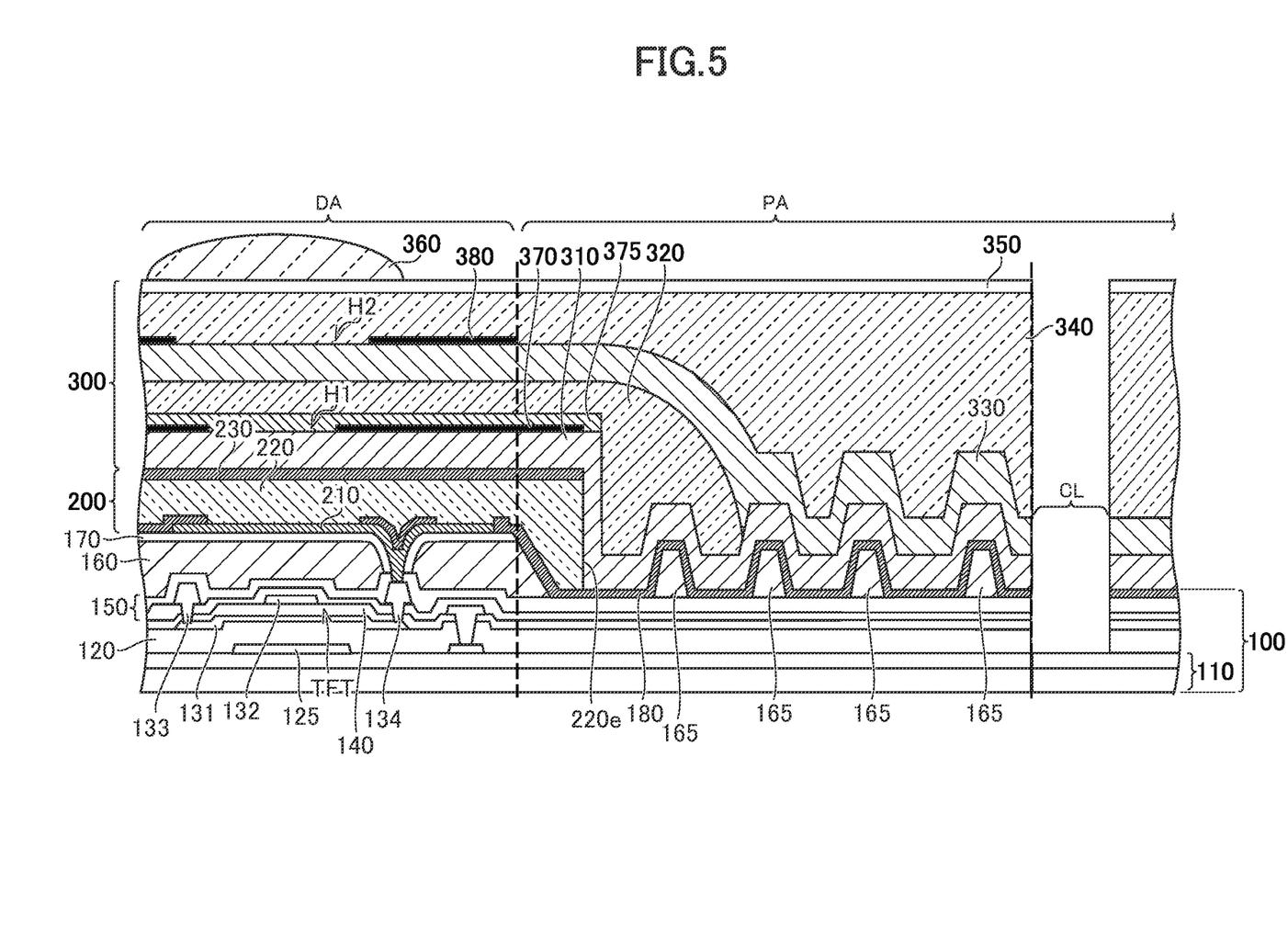
FIG. 5 is a cross-sectional view of a sensing device according to a third modification.
Figure 6:
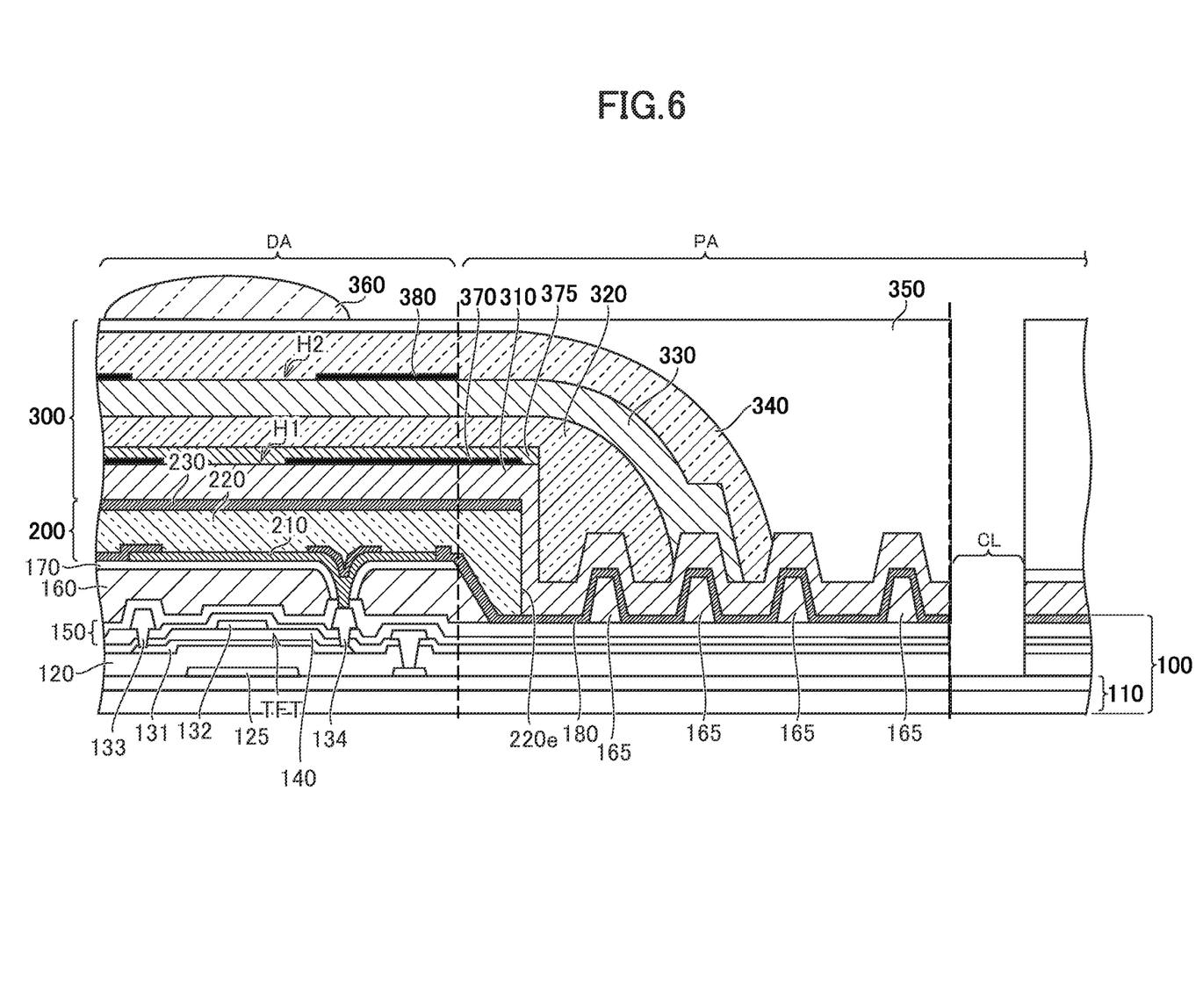
FIG. 6 is a cross-sectional view of a sensing device according to a fourth modification.
Figure 7:
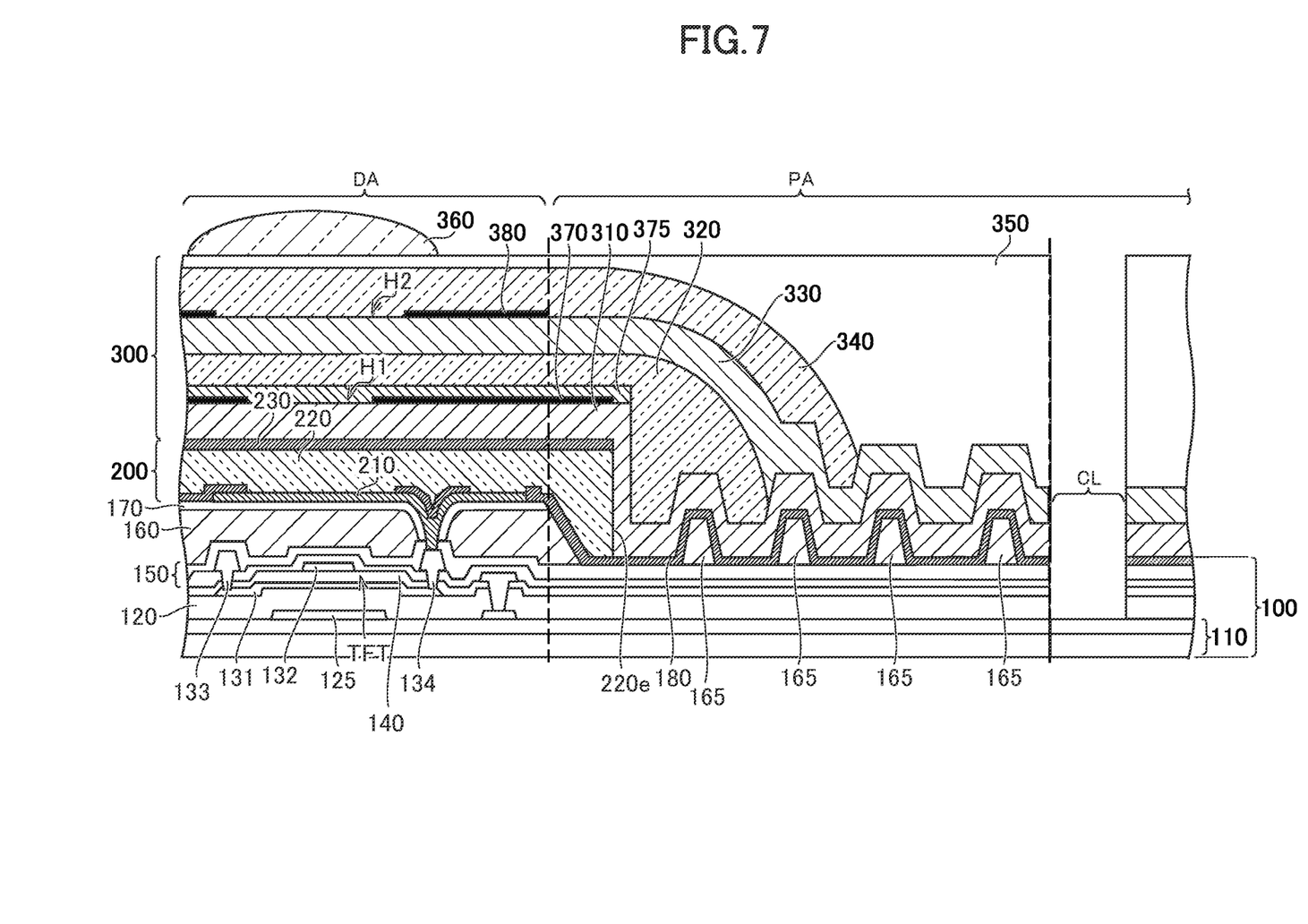
FIG. 7 is a cross-sectional view of a sensing device according to a fifth modification.

Referring to FIGS. 5 to 7, a sensing device according to other modifications of the present embodiment will be described. FIG. 5 is a cross-sectional view of a sensing device according to the third modification. FIG. 6 is a cross-sectional view of a sensing device according to the fourth modification. FIG. 7 is a cross-sectional view of a sensing device according to the fifth modification. FIGS. 5 to 7 show a part corresponding to the cross-sectional views shown in FIGS. 2 and 3. The layers having the same functions as the layers described with reference to FIGS. 2 and 3 are denoted by the same reference signs, and the detailed explanation thereof is omitted. In the following, the configuration different from the configuration described with reference to FIGS. 2 and 3 will be mainly described.

As shown in FIG. 5, the sensing device according to the third modification includes the wall portion 165 formed therein similarly to the sensing device 1 shown in FIG. 2. The first inorganic layer 310 and the second inorganic layer 330 are in contact with each other in the frame area PA. The sensing device according to the third modification is different from the sensing device 1 shown in FIG. 2 in that the second transparent resin layer 340 covers the second inorganic layer 330 provided along the wall portion 165 and extends outward of the cut line CL. The foundation layer 350 is provided above the second transparent resin layer 340 and extends outward of the cut line CL. Accordingly, the thickness of the frame area PA is substantially the same as the thickness of the detection area DA.

As shown in FIG. 6, in the sensing device according to the fourth modification, the wall portion 165 is formed similarly to the sensing device 1 shown in FIG. 3. In the frame area PA, the first inorganic layer 310 and the second inorganic layer 330 are in contact with each other. The sensing device according to the fourth modification is different from the sensing device 1 shown in FIG. 3 in that the foundation layer 350 covers the first inorganic layer 310 provided along the wall portion 165 and extends to the outer side of the cut line CL. Accordingly, the thickness of the frame area PA is substantially the same as the thickness of the detection area DA. In the fourth modification, the foundation layer 350 may be made of an organic material.

As shown in FIG. 7, the sensing device according to the fifth modification includes the wall portion 165 formed therein similarly to the sensing device 1 shown in FIG. 2. The first inorganic layer 310 and the second inorganic layer 330 are in contact with each other in the frame area PA. In the sensing device according to the fifth modification, the foundation layer 350 covers the second inorganic film 330 provided along the wall portion 165 and extends outward of the cut line CL. Accordingly, the thickness of the frame area PA is substantially the same as the thickness of the detection area DA In the fifth modification, the foundation layer 350 may be made of an organic material.

[Upper Substrate]

Figure 8A:
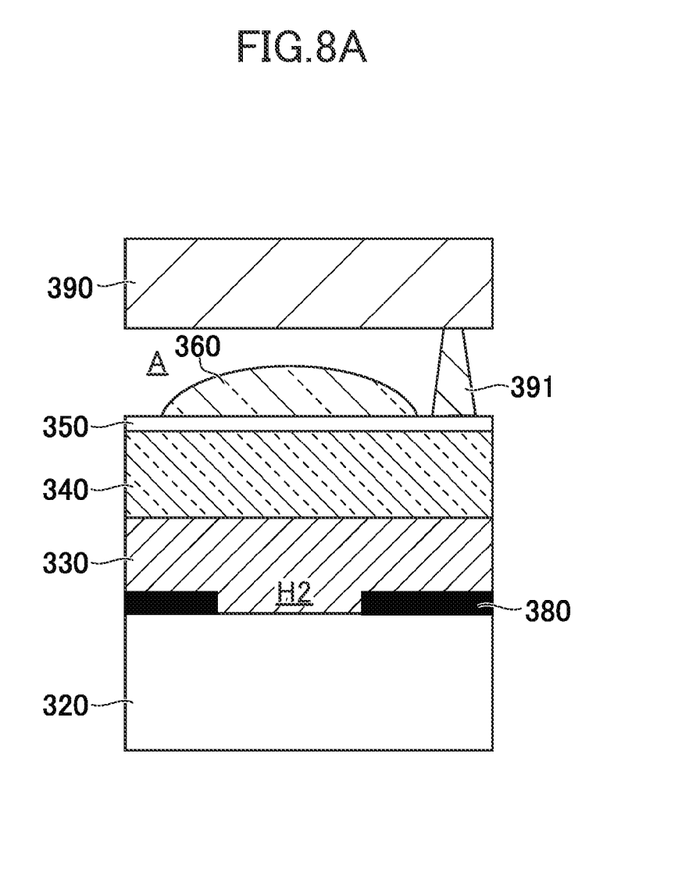
FIG. 8A is a schematic diagram illustrating an example of a laminate structure on a microlens.
Figure 8B:
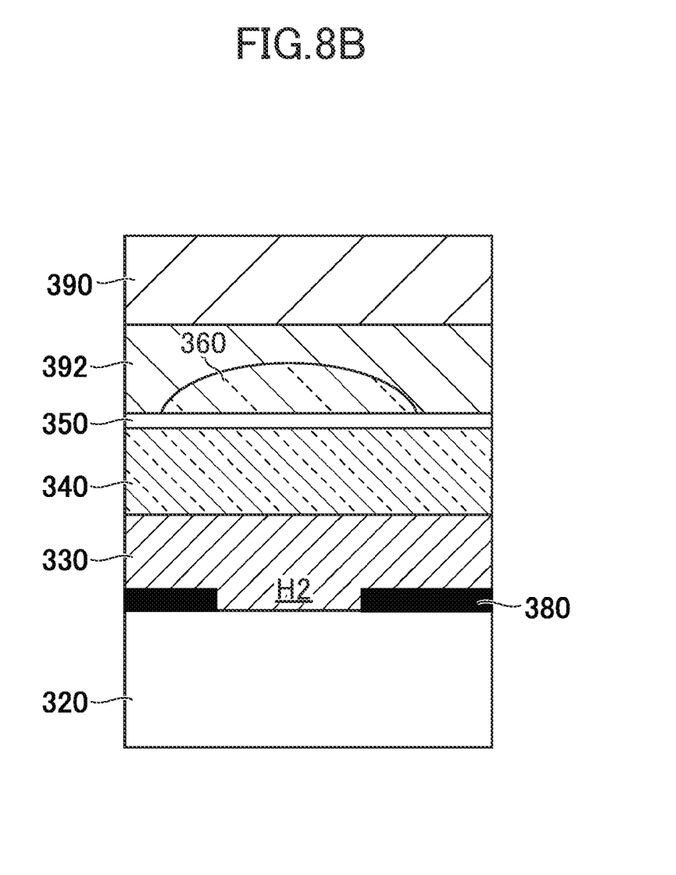
FIG. 8B is a schematic diagram illustrating an example of a laminate structure on a microlens.
Figure 8C:
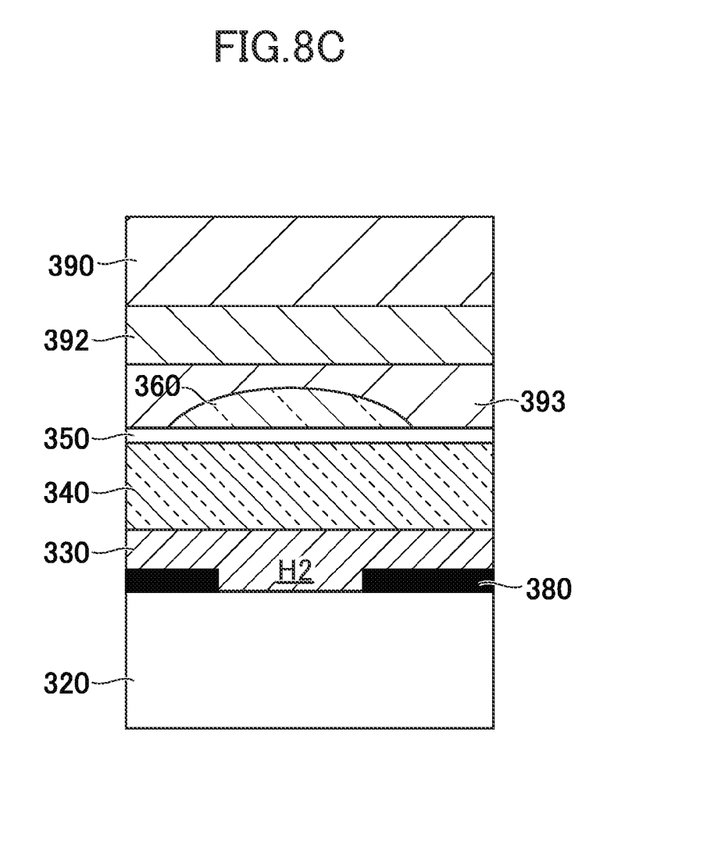
FIG. 8C is a schematic diagram illustrating an example of a laminate structure on a microlens.

Referring to FIGS. 8A to 8C, a laminate structure above the microlens 360 will be described. FIGS. 8A to 8C are schematic diagrams showing examples of laminate structures on the microlens. As shown in FIGS. 8A to 8C, an upper substrate 390 may be provided above the microlens 360. The upper substrate 390 may be a protective substrate for the microlens 360 or a scintillator for performing wavelength conversion, for example.

FIG. 8A shows an example of a spacer 391 that extends in the film thickness direction and forms an air layer A between the microlens 360 and the upper substrate 390. The lower edge of the spacer 391 is provided above the foundation layer 350, and the upper edge of the spacer 391 is provided above the lower surface of the upper substrate 390.

FIG. 8B shows an example in which an optical clear adhesive (OCA) sheet 392 is used to attach the upper substrate 390 to the microlens 360.

FIG. 8C shows an example in which the microlens 360 is covered with a protective layer 393 and the upper substrate 390 is attached to the protective layer 393 using the optical clear adhesive sheet 392.

The configurations shown in FIGS. 8A to 8C may be applied to the sensing device 1 according to the present embodiment and the modifications described above.

[Others]

In the present embodiment and the modifications thereof, the example has been described in which the foundation layer 350 is provided in the sealing structure 300 so as to provide the microlens 360, although the present invention is not limited thereto. The foundation layer 350 may not be provided and the microlens 360 may be directly provided above the second transparent resin layer 340. Further, the microlens 360 may not be essential.

In the present embodiment and the modifications thereof, two light shielding layers are provided, although the present invention is not limited thereto and three or more layers may be provided. In this case, the number of transparent resin layers and inorganic layers may be increased in the sealing structure 300 according to the total number of the light shielding layers.

In FIGS. 2 to 7, the end portions of the respective layers included in the sealing structure 300 are positioned in the frame area PA, although the present invention is not limited thereto. An end portion of the layer formed of an inorganic material included in the sealing structure 300 may be positioned at least outward of the end portion 220e of the organic layer 220. In other words, the end portion of the layer included in the sealing structure 300 may be positioned in the detection area DA.

The sealing structure 300 may not include the second inorganic layer 330 if the first inorganic layer 310 has sufficient sealing performance. The sealing structure 300 may further include a transparent resin layer and an inorganic layer above the second inorganic layer 330.

Although not shown, the sensing device 1 may include a display panel, such as an organic EL display, above the sealing structure 300.

While there have been described what are at present considered to be certain embodiments of the invention, it will be understood that various modifications may be made thereto, and it is intended that the appended claims cover all such modifications as fall within the true spirit and scope of the invention.

What is claimed is:

1. A sensing device comprising:
   a substrate
   a light detection sensor including a plurality of pixels disposed in a matrix, a lower electrode, an organic layer provided above the lower electrode, and an upper electrode provided above the organic layer, wherein each of the pixels receives light reflected by a detection object or light transmitted through the detection object;
   a sealing structure that includes a first inorganic layer provided above the light detection sensor and an inorganic insulating layer below the organic layer; and
   a collimator that is provided above the light detection sensor and blocks a part of light incident on the light detection sensor, and includes a first light shielding layer provided above the first inorganic layer,
   wherein
   the first light shielding layer includes a first opening permitting entry of light into the light detection sensor,
   a distance between the light detection sensor and the first light shielding layer is adjustable based on a thickness of the first inorganic layer, and
   an end portion of the organic layer is covered by the first inorganic layer and the inorganic insulating layer.

2. The sensing device according to claim 1, wherein
the sealing structure includes a first resin layer provided above the first inorganic layer and a second inorganic layer provided above the first resin layer, and
an end portion of the second inorganic layer is positioned outward of the end portion of the organic layer.

3. The sensing device according to claim 2, wherein
the end portion of the second inorganic layer is in contact with the first inorganic layer.

4. The sensing device according to claim 2, wherein
the sealing structure includes a second resin layer provided above the second inorganic layer.

5. The sensing device according to claim 4, wherein
the layer thickness adjustment layer includes the first inorganic layer, the first resin layer, the second inorganic layer, and the second resin layer.

6. The sensing device according to claim 1 comprising a wall portion that is disposed outward of the end portion of the organic layer and forms unevenness, wherein
the first inorganic layer is provided so as to cover the wall portion.

7. The sensing device according to claim 6, wherein
a plurality of the wall portions are disposed in an outward direction.

8. The sensing device according to claim 6, wherein
the first inorganic layer covers the wall portions and is formed so as to be along a shape of at least a part of the wall portions.

9. The sensing device according to claim 8, wherein
the sealing structure includes the second inorganic layer provided above the first resin layer, and
the second inorganic layer is formed so as to be along the shape of at least a part of the plurality of wall portions.

10. The sensing device according to claim 1, wherein
the collimator further includes a second light shielding layer that is provided above the first light shielding layer and the second light shielding layer includes a second opening permitting entry of light into the light detection sensor, the second opening being larger than the first opening.

11. The sensing device according to claim 1, wherein
the collimator further includes a lens that is provided above the first light shielding layer so as to overlap the first opening in a plan view.

12. The sensing device according to claim 11, wherein
the sealing structure includes a foundation layer on which the lens is provided.

13. The sensing device according to claim 12, wherein
the foundation layer is made of an inorganic material.

14. The sensing device according to claim 13, wherein
an end portion of the foundation layer is positioned outward of the end portion of the organic layer.

15. The sensing device according to claim 14, wherein
the end portion of the foundation layer is in contact with the first inorganic layer.

16. The sensing device according to claim 1 comprising:
a detection area in which the light detection sensor is disposed; and
a frame area positioned outward of the detection area, wherein
the end portion of the first inorganic layer is positioned in the frame area.

17. The sensing device according to claim 1, wherein the collimator further includes a lens provided above the first light shielding layer so as to overlap the first opening in a plan view, and
a width of the lens is wider than the width of the first opening in a cross-sectional view.

* * * * *